United States Patent [19]

Rivier et al.

[11] 4,244,946
[45] Jan. 13, 1981

[54] WATER-SOLUBLE PEPTIDES AFFECTING GONADAL FUNCTION

[75] Inventors: Jean E. F. Rivier; Wylie W. Vale, Jr., both of La Jolla, Calif.

[73] Assignee: The Salk Institute for Biological Studies, San Diego, Calif.

[21] Appl. No.: 47,026

[22] Filed: Jun. 11, 1979

[51] Int. Cl.$^3$ .................... A61K 37/00; C07C 103/52
[52] U.S. Cl. ............................ 424/177; 260/112.5 LH
[58] Field of Search ............... 424/177; 260/112.5 LH

[56] References Cited

U.S. PATENT DOCUMENTS

| | | | |
|---|---|---|---|
| 4,010,125 | 3/1977 | Schally et al. | 260/112.5 LH |
| 4,018,726 | 4/1977 | Schally et al. | 260/112.5 LH |
| 4,034,082 | 7/1977 | Johnson et al. | 424/177 |
| 4,086,219 | 4/1978 | Wittle et al. | 260/112.5 LH |

OTHER PUBLICATIONS

J. Rivier, et al., "Peptides", 1976, pp. 427–451.

Primary Examiner—Delbert R. Phillips
Attorney, Agent, or Firm—Fitch, Even, Tabin, Flannery & Welsh

[57] ABSTRACT

[im-Bzl D-His$^6$]LRF and [D-His$^6$(im-Bzl), Pro$^9$-NEt]LRF exhibit hydrophillicity comparable to that of LRF and act as superagonists exhibiting potencies, respectively, about 12 and more than 200 times that of LRF. The peptides or their nontoxic salts can be administered by intravenous subcutaneous, sublingual, oral, intravaginal, intranasal or rectal routes. The peptides can be used to regulate fertility in male and female mammals, including human beings.

6 Claims, No Drawings

WATER-SOLUBLE PEPTIDES AFFECTING GONADAL FUNCTION

The invention described herein was made in the course of work under a grant or award from the Department of Health, Education, and Welfare.

The present invention relates to peptides which influence the release of gonadotropins by the pituitary gland in mammalians, including humans. More particularly, the present invention is directed to peptides which when administered acutely to mammalians exhibit increased potency in releasing gonadotropins, which subsequently cause the release of the steroidal hormones, progesterone, testosterone and estrogens.

The pituitary gland is attached to a stalk to the region in the base of the brain known as the hypothalamus and has two principal lobes, the anterior lobe and the posterior lobe. The posterior lobe of the pituitary gland stores and passes onto the general circulation system two hormones manufactured in the hypothalamus, i.e., vasopressin and oxytocin. The anterior lobe of the pituitary gland secretes a number of hormones, which are complex protein or glycoprotein molecules, that travel through the blood stream to various organs and which, in turn, stimulate the secretion into the blood stream of other hormones from the peripheral organs. In particular, follicle stimulating hormone (FSH) and luteinizing hormone (LH), sometimes referred to as gonadotropins or gonadotropic hormones, are released by the pituitary gland. These hormones, in combination, regulate the functioning of the gonads to produce testosterone in the testes and progesterone and estrogen in the ovaries, and also regulate the production and maturation of gametes.

The release of a hormone by the anterior lobe of the pituitary gland usually requires a prior release of another class of hormones produced by the hypothalamus. Such a hypothalamic hormone acts as a factor that triggers the release of the gonadotropic hormones, particularly luteinizing hormone (LH). The particular hypothalamic hormone which acts as a releasing factor for the gonadotropins LH and FSH is referred to herein as LRF, wherein RF stands for "releasing factor" and L signifies that one hormone released is LH. LRF has been isolated, identified and synthesized.

It has been demonstrated that some female mammalians who have no ovulatory cycle and who show no pituitary or ovarian defect begin to secrete normal amounts of the gonadotropins LH and FSH after the administration of LRF. Such administration of LRF is suitable for the treatment of those cases of infertility where the functional defect resides in the hypothalamus. Ovulation can also be induced in female mammalians by the administration of LRF; however, the dosage level of LRF required to influence ovulation may sometimes be high. Recent reports have also indicated that the administration of large and frequent dosages of LRF actually inhibit gonadal function in female and male rats by desensitization of the pituitary and gonads and subsequent disruption of the hormonal network. For this reason, LRF and analogs of LRF which are more potent than LRF to promote release of LH have been investigated for potential use as a contraceptive. The principal disadvantage to the use of these peptides as a potential contraceptive is, of course, the requirement for large and frequent dosages. It would be desirable to provide peptides which are many times more potent than LRF in promoting the secretion of LH.

Accordingly, it is a principal object of the present invention to provide peptides which exhibit a very high potency to cause the release of gonadotropins in mammalians, including humans. Another object of the present invention is to provide such potent peptides which influence the release of steroids by the gonads of male and female mammalians, including humans, and which have properties which favorably affect their administration. A further object of the present invention is to provide peptides which have a more potent effect than LRF on the reproduction processes of mammalians, including humans. These and other objects of the present invention will become more apparent from the following detailed description.

Generally, in accordance with the present invention, LRF agonists have been synthesized which have an enhanced potency to cause the secretion of gonadotropins by the pituitary gland of mammalians, including humans, and which peptides also can cause inhibition of the reproductive functions in both males and females, such as delay of puberty, interruption of pregnancy, decrease in sexual organ weights and steroid production, and disrupted spermogenesis. The peptides of the present invention are characterized by the substitution of (im-Bzl) D-His in the 6-position of LRF or an LRF analog.

LRF has been characterized as a decapeptide having the following structure:

p-Glu-His-Trp-Ser-Tyr-Gly-Leu-Arg-Pro-Gly-NH$_2$

Peptides are compounds which contain two or more amino acids in which the carboxyl group of one acid is linked to the amino group of the other acid. The formula for LRF, as represented above, is in accordance with conventional representation of peptides where the amino group appears to the left and the carboxyl group to the right. The position of the amino groups is identified by numbering the amino groups from left to right. In the case of LRF, the hydroxyl portion of the carboxyl group at the right-hand end has been replaced with an amino group (NH$_2$), to give an amide function. The abbreviations for the individual amino acid groups above are conventional and are based on the trivial name of the amino acid: where p-Glu is pyroglutamic acid, His is histidine, Trp is tryptophan, Ser is serine, Tyr is tyrosine, Gly is glycine, Leu is Leucine, Arg is arginine and Pro is proline. Except for glycine, amino acid residues in the peptides of the invention should be understood to be of the L-configuration unless noted otherwise.

It is known that the substitution of a D-amino acid (for example D-Trp) for Gly in the 6-position of the LRF decapeptide provides a peptide material having from about 10 to 30 times greater potency than does LRF to effect the release of luteinizing hormone and other gonadotropins by the pituitary gland of mammalians. The releasing effect is obtained when the substituted peptide is introduced into the blood stream of a mammalian. The desired peptides are not significantly different in their hydrophilicity from LRF, whereas other potent LRF analogs are significantly less hydrophilic, and this will provide opportunities for administration in various ways including those most suitable for peptides having a longer duration of effect.

In accordance with the present invention, peptides have been synthesized which are highly potent to release gonadotropins and are represented by the following formula:

p-Glu-His-Trp-Ser-Tyr-D-His(im-Bzl)-Leu-Arg-R wherein R is selected from the group consisting of Pro-Gly-$NH_2$ and Pro-NH-$CH_2$-$CH_3$. D-His(im-Bzl) refers to imidazole benzyl D-histidine wherein the benzyl group is attached to one of the nitrogen atoms in the imidazole ring of the histidine residue.

The peptides of the present invention having D-His-(im-Bzl) in the 6-position have greatly enhanced potency compared to other known LRF analogs which have been reported earlier, for example in U.S. Pat. Nos. 3,896,104, 3,972,859 and 4,034,082. The enhanced potency of these LRF agonists and the fact that they are substantially more hydrophilic than other analogs renders them of significant value in treating both male and female infertility and also in the inhibition of reproductive functions in both males and females as a result of long-term administration.

The peptides of the present invention are synthesized by a solid phase technique. The synthesis is preferably conducted in a stepwise manner on a chloromethylated resin when R is Pro-NH-$CH_2$-$CH_3$ and on a benzhydrylamine or a methyl-benzhydrylamine resin when R is Pro-Gly-$NH_2$. However, a chloromethylated resin may also be used when R is Pro-Gly-$NH_2$ because aminolysis of the glycine benzyl ester can be achieved using ammonia. The resin is composed of fine beads (20–70 microns in diameter) of a synthetic resin prepared by copolymerization of styrene with 1 to 2 percent divinylbenzene. For a chloromethylated resin, the benzene rings in the resin are chloromethylated in a Friedel-Crafts reaction with chloromethyl ether and stannic chloride, and the chlorine introduced is a reactive benzyl chloride. The Friedel-Crafts reaction is continued until the resin contains 0.5 to 2 millimoles of chlorine per gram of resin. The benzhydrylamine resin is prepared in accordance with the teaching of U.S. Pat. No. 4,072,688 issued Feb. 7, 1976 to Max S. Amoss et al. More recently, a paramethyl-BHS has been used, which may be obtained as generally described in U.S. Pat. No. 4,072,688 with the exception that p-toluolyl chloride is used instead of benzyl chloride in the Friedel-Crafts step. Mild conditions during HF cleavage can be used with such a resin, and as a result, a purer peptide is obtained than the equivalent one made on regular BHA.

The reagents used are hereinbelow first listed by their chemical name and their common abbreviation.

A peptide wherein R is Pro-NH-$CH_2$-$CH_3$ or Pro-Gly-$NH_2$, may be prepared, for example by esterifying the triethylammonium salt of α-amino protected Pro or Gly onto the chloromethylated resin by refluxing in ethanol for about 48 hours. Also possible is the use of α-amino protected Pro, potassium or cesium salts in dimethylformamide (DMF) or in dimethylsulfoxide (DMS), at temperatures ranging from 40° to 80° C. Further possible is the use of the α-amino protected Pro dissolved in DMF in combination with the chloromethylated resin in the presence of KF. After deprotection of the α-amino N-terminus and neutralization, the stepwise addition of N-protected amino acids is effected as generally taught in Monahan, et al. Biochemistry (1963) Volume 12, P. 4616–4620. The $N^\alpha$ groups may be protected by t-butoxycarbonyl (BOC) and the side chain of Arg may be protected with p-toluenesulfonyl (Tos). Benzyl ester (OBzl) may be used as a side chain protecting group for Ser and Tyr. 2-6 dichlorobenzyl may be used as the side chain protecting group for Tyr; and Tos, dinitrophenyl (Dnp) or BOC can be used as the side chain protecting group for His. pGlu may be introduced, for example, as benzyloxycarbonyl (Z) protected amino acid, or without any protection.

Such a method provides the fully protected peptidoresin, and the fully protected peptide is removed from the resin support in a suitable manner, e.g., using ammonia or by aminolysis employing dimethylamine, methylamine, ethylamine, n-propylamine, i-propylamine, butylamine, iso-butylamine, pentylamine or phenethylamine to yield a fully protected alkyl amide intermediate. As one example, cleavage of the peptide from the resin may be performed by stirring the peptidoresin (. . . Pro-O-$CH_2$-resin) overnight in distilled ethylamine at 0° C. in a pressure bottle. As another example, the peptidoresin (. . . Pro-Gly-O-$CH_2$-resin) may be treated for several days in dry methanol which is kept saturated with $NH_3$ by bubbling gaseous ammonia therethrough. After removal of excess ethylamine or methanolic ammonia by distillation under nitrogen or vacuum, the resin, suspended in methanol, is removed from the slurry by filtration. The resin is further washed successively with dimethylformamide (DMF), methanol, and a mixture of DMF and methanol. The recovered solution of cleaved, protected peptide is evaporated to dryness on a rotary vacuum evaporator at room temperature. The peptide is taken in a minimum amount of methanol to dissolve the peptide. The solution is added dropwise with stirring to a 200-times volume excess of dry ether. A flocculent precipitate appears which is recovered by filtration or centrifugation. The recovered precipitate is dried to provide the intermediate which is considered part of the invention.

The intermediates of the invention may be represented as:

$X^1$-p-Glu-His($X^2$)-Trp-Ser($X^3$)-Tyr($X^4$)-D-His(im-Bzl)-Leu-Arg($X^5$)-Pro-$X^6$ wherein: $X^1$ is either hydrogen or an α-amino protecting group of the type known to be useful in the art in the stepwise synthesis of polypeptides. Among the classes of α-amino protecting groups covered by $X^1$ are (1) acyl-type protecting groups, such as formyl, trifluoroacetyl, phthalyl, Tos, benzensulfonyl, nitrophenylsulfenyl, tritylsulfenyl, o-nitrophenoxyacetyl, chloroacetyl, acetyl and y-chlorobutyrul; (2) aromatic urethan-type protecting groups, e.g., benzyloxycarbonyl and substituted benzyloxycarbonyl, such as p-chlorobenzyloxycarbonyl, p-nitrobenzyloxycarbonyl, p-bromobenzyloxycarbonyl and p-methoxybenzyloxycarbonyl; (3) aliphatic urethan protecting groups, such as BOC, diisopropylmethoxycarbonyl, isopropyloxycarbonyl, ethoxycarbonyl and allyloxycarbonyl; (4) cycloalkyl urethan-type protecting groups, such as cyclopentyloxycarbonyl, adamantyloxycarbonyl and cyclohexyloxycarbonyl; (5) thiourethan-type protecting groups, such as phenylthiocarbonyl; (6) alkyl-type protecting groups, such as triphenylmethyl (trityl) and benzyl; (7) trialkylsilane groups, such as trimethylsilane. The preferred α-amino protecting group is BOC.

$X^2$ is a protecting group for the imidazole nitrogen atom selected from the group consisting of Tos, benzyl, trityl, 2,2,2-trifluoro-1-benzyloxycarbonylaminoethyl, 2,2,2,-trifluoro-1-tert-butyloxycarbonylaminoethyl and 2,4-dinitrothiophenyl.

$X^3$ is a protecting group for the alcoholic hydroxyl group of Ser and is selected from the group consisting of acetyl, benzoyl, tetrahydropyranyl, tert-butyl, trityl, benzyl and 2,6-dichlorobenzyl and preferably is benzyl.

$X^4$ is a protecting group for the phenolic hydroxyl group of Tyr selected from the group consisting of tetrahydropyranyl, tert-butyl, trityl, benzyl, benzyloxycarbonyl, 4-bromobenzyloxycarbonyl and 2,6-dichlorobenzyl.

$X^5$ is a protecting group for the nitrogen atoms of Arg and is selected from the group consisting of nitro, Tos, benzyloxycarbonyl, adamantyloxycarbonyl; and BOC; or is hydrogen which means there are no protecting groups on the side chain nitrogen atoms of arginine.

$X^6$ is selected from dimethylamine, alkylamine of 1 to 5 carbon atoms, phenethylamine, O-CH$_2$-[resin support] or Gly-O-CH$_2$-[resin support] or Gly-NH [resin support].

The criterion for selecting side chain protecting groups for $X^2$-$X^5$ are that the protecting group must be stable to the reagent under the reaction conditions selected for removing the α-amino protecting group at each step of the synthesis, the protecting group must not be split off under coupling conditions and the protecting group must be removable upon completion of the synthesis of the desired amino acid sequence under reaction conditions that will not alter the peptide chain.

When the $X^6$ group is -O-CH$_2$-[resin support] or Gly-O-CH$_2$-[resin support], what is represented is the ester moiety of one of the many functional groups of the polystyrene resin support. When the $X^6$ group is Gly-NH-[resin support], an amide bond connects Gly to benzhydrylamine resin or to methyl benzhydrylamine resin.

For the preparation of a peptide wherein R is Pro-Gly-NH$_2$ on a benzhydrylamine resin, N-termini and side chain protecting groups as generally defined above are used for the synthesis. Coupling of the Gly residue is carried out for 1 to 5 hours in methylenechloride (CH$_2$Cl$_2$), dimethylformamide (DMF) or mixtures thereof, using a 2-5 fold excess of BOC-protected amino acid and dicylcohexylcarbodiimide (DCC) activating reagent. The first residue is attached to the benzhydrylamine resin by an amide bond. The coupling reaction throughout the synthesis is monitored by a ninhydrin test, as reported by Kaiser et al. *Anal. Biochem.* 34 (1970) 595.

Deblocking is effected by a 20-minute treatment in TFA containing 5 percent 1,2-ethanedithiol, followed by neutralization with triethylamine (Et$_3$N) in DMF or methylene chloride. Numerous washes with MeOH and CH$_2$Cl$_2$ follow each step. The individual amino aid residues are added sequentially to complete the peptide chain.

Deprotection of the peptides and/or cleavage of the peptide from a benzhydrylamine resin or paramethyl-BHA resin may take place at 0° C. with hydrofluoric acid (HF) or other suitable reagent. Anisole or some other appropriate scavenger, e.g., methyl anisole or thioanisole, is preferably added to the peptide prior to treatment with HF. After the removal of HF, under vacuum, the cleaved, deprotected peptide is treated with ether, filtered, extracted in dilute acetic acid, separated from the resin by filtration and lyophilized.

Purification of the peptide may be effected by ion exchange chromatography on a carboxyl methyl cellulose (CMC) column, followed by partition chromatography on a gel filtration column using the elution system: n-butanol; acetic acid; water (4:1:5; volume ratio). Sephadex G 25 may be the partition chromatography column packing, and other cation exchange, such as CM-Sephadex or counter-current distribution, can also be used for the purification.

The peptides are used at a level effective to promote ovulation in female mammals and can also be used for other pharmaceutical purposes for which LRF has heretofore been employed. Because the potency of the peptides of the invention is about 12 and 217 times that of LRF (see Table I, hereinafter) the dosage may be determined for each application on the basis of such a ratio, taking other factors such as the subject of administration into consideration. For example, a suitable dosage may be within the range of about 5 ng. (nanograms) to 10 μg. daily, per kilogram of body weight.

The peptide can be administered to mammals intravenously, subcutaneously, intramuscularly, intranasally, vaginally, orally or sublingually. The effective dosage will vary with the form of administration and the particular species of mammal to be treated. Oral administration may be in either solid or liquid form.

Because the peptides of the invention exhibit hydrophillicity comparable to that of LRF, higher concentrations can be prepared in aqueous or saline solutions which provide significant advantages in administration over the other superagonist analogs reported thus far. A most important advantage lies in the fact that such an aqueous peptide solution can be administered intranasally.

The peptide may also be prepared and administered in the form of a pharmaceutically acceptable nontoxic salt, such as an acid-addition salt, or an appropriate metal complex, e.g., with zinc, iron or the like. Illustrative of pharmaceutically acceptable non-toxic salts of peptides are hydrochloride, hydrobromide, sulfate, phosphate, maleate, acetate, citrate, benzoate, succinate, malate, ascorbate, and the like.

The following Examples further illustrate various features of the invention but are intended to in no way limit the scope of the invention which is defined in the appended claims.

EXAMPLE I

[im-Bzl D-His$^6$]-LRF having the following formula is prepared by the solid phase synthesis: p-Glu-His-Trp-Ser-Tyr-D-His(im-Bzl)-Leu-Arg-Pro-Gly-NH$_2$.

A paramethyl benzhydrylamine resin is used, and BOC-protected Gly is coupled to the resin over a 2-hour period in CH$_2$Cl$_2$ using a 3-fold excess of the BOC reagent and dicyclohexlcarbodiimide (DCC) as an activating reagent. This attaches the glycine residue to the benzhydrylamine residue by an amide bond.

Following the coupling of each amino acid residue, washing, deblocking and coupling of the next amino acid residue is carried out in accordance with the following schedule using an automated machine and beginning with about 5 grams of resin:

| Step | Reagents and Operations | Mix Times Min. |
| --- | --- | --- |
| 1 | CH$_2$Cl$_2$ wash 80 ml. (2 times) | 3 |
| 2 | Methanol (MeOH) wash 30 ml. (2 times) | 3 |
| 3 | CH$_2$Cl$_2$ wash 80 ml. (3 times) | 3 |
| 4 | 50 percent trifluoroacetic acid (TFA) plus 5 percent 1,2-ethanedithiol in CH$_2$Cl$_2$ 70 ml. (2 times) | 10 |
| 5 | CH$_2$Cl$_2$ wash 80 ml. (2 times) | 3 |
| 6 | Triethylamine (Et$_3$N) 12.5 percent in 70 ml. of CH$_2$Cl$_2$ (2 times) | 5 |
| 7 | MeOH wash 40 ml. (2 times) | 2 |
| 8 | CH$_2$Cl$_2$ wash 80 ml. (3 times) | 3 |
| 9 | BOC-amino acid (10 mmoles) in 30 ml. of either DMF or CH$_2$Cl$_2$. | |

-continued

| Step | Reagents and Operations | Mix Times Min. |
|------|------------------------|----------------|
|      | depending upon the solubility of the particular protected amino acid, (1 time) plus dicyclohexylcarbodiimide (DCC) (10 mmoles) in CH$_2$Cl$_2$ | 30–300 |
| 10   | MeOH wash 40 ml. (2 times) | 3 |
| 11   | Et$_3$N 12.5 percent in CH$_2$Cl$_2$ 70 ml. (1 time) | 3 |
| 12   | MeOH wash 30 ml. (2 times) | 3 |
| 13   | CH$_2$Cl$_2$ wash 80 ml. (2 times) | 3 |

After step 13, an aliquot is taken for a ninhydrin test: if the test is negative, go back to step 1 for coupling of the next amino acid; if the test is positive or slightly positive, go back and repeat steps 9 through 13.

The above schedule is used for coupling of each of the amino acids of the peptide of the invention after the first amino acid has been attached. N$^\alpha$ BOC protection is used for each of the remaining amino acids throughout the synthesis. The side chain of Arg is protected with Tos. OBzl is used as a side chain protecting group for the hydroxyl group of Ser, and 2-6 dichlorobenzyl is used as the side chain protecting group for the hydroxyl group of Tyr. p-Toluenesulfonyl (Tos) is used as the side chain protecting group for His at the 2-position, but D-His(im-Bzl) does not require side-chain protection. pGlu is introduced as the benzyloxycarbonyl (Z) protected amino acid or as plain p-Glu. The following amino acids, which have low solubility in CH$_2$Cl$_2$, are coupled using DMF: BOC-Arg(Tos); BOC-Trp; Z-pGlu or pGlu; and D-His(im-Bzl).

The cleavage of the peptide from the resin and complete deprotection of the side chains with the exception of (im-Bzl) of D-His$^6$ takes place very readily at 0° C. with hydrofluoric acid (HF). Anisole is added as a scavenger prior to HF treatment. After the removal of HF under vacuum, the resin is extracted with 0.1% acetic acid, and the washings are lyophilized to provide a crude peptide powder.

Purification of the peptide is then effected by ion exchange chromatography on carboxymethyl cellulose (Whatman CM 32, using a step gradient of 0.125 M NH$_4$OAc) followed by partition chromatography in a gel filtration column using the elution system: n-Butanol; Acetic acid; Water (4:1:5--volume ratio).

[D-His$^6$(im-Bzl)]-LRF is judged to be homogeneous using thin layer chromatography with several different solvent systems and using reversed-phase high pressure liquid chromatography as generally taught in Rivier, "Use of Trialkyl Ammonium Phosphate (TAAP) Buffers in Reverse Phase HPLC for High Resolution and High Recovery of Peptides and Proteins", *Journal of Liquid Chromatography*, 1(3), 343–366 (1978) and employing an aqueous triethylammonium phosphate buffer plus acetonitrile as the solvent system. Amino acid analysis of the resultant, purified peptide is consistent with the formula for the prepared structure, showing substantially integer-values for each amino acid in the chain. Nuclear magnetic resonance spectra is also consistent and shows the presence of the benzyl group. The optical rotation is measured on a photoelectric polarimeter $[\alpha]_D^{22} = -26.0°$ (c=1, 1% acetic acid).

EXAMPLE II

The LRF analog [D-His$^6$(im-Bzl), Pro$^9$-NEt]-LRF is synthesized by solid phase technique in a stepwise manner on a chloromethylated resin prepared by the copolymerization of styrene with about 1% divinylbenzene.

The triethylammonium salt of BOC-protected Pro is esterified onto the chloromethylated resin by refluxing in ethanol for about 48 hours. After deprotection and neutralization, the BOC-derivative of the next amino acid, Arg, and each successive amino acid, is added in accordance with the procedure set forth in Example I.

The fully protected peptide is removed from the resin support by aminolysis employing ethylamine to yield the fully protected alkyl amide intermediate. Cleavage of the peptide is performed by stirring the resin overnight in distilled ethylamine at 0° C. in a pressure bottle. After removal of excess ethylamine by distillation under vacuum, the resin, suspended in methanol, is removed from the slurry by filtration. The resin is further washed successively with DMF, methanol, and a mixture of DMF and methanol. The recovered solution of cleaved, protected peptide is evaporated to dryness on a rotary vacuum evaporator at room temperature. Using a minimum amount of methanol to dissolve the peptide, the solution is added dropwise to a 250-times volume excess of dry ether with stirring. A flocculent precipitate appears and is recovered by centrifugation. The recovered precipitate is dried to provide the intermediate, which is then completely deprotected using HF as earlier described.

Purification of the peptide is effected by ion exchange chromatography on a CMC column, followed by partition chromatography using the elution system: n-butanol; acetic acid; water (4:1:5—volume ratio). The partition chromatography column is Sephadex G 25.

[D-His$^6$(im-Bzl)Pro$^9$NEt]-LRF is judged to be homogeneous using thin layer chromatography and several different solvent systems, as well as by using reversed-phase high pressure liquid chromatography and an aqueous triethylammonium phosphate solution plus acetonitrile. Amino acid analysis of the resultant, purified peptide is consistent with the formula for the prepared structure, showing substantially integer-values for each amino acid in the chain. Nuclear magnetic resonance spectra is also consistent and shows the presence of the benzyl group. The optical rotation is measured on a photoelectric polarimeter $[\alpha]_D^{22} = -33.9°$ (c=1, 1% acetic acid).

The peptides prepared in the foregoing Example I are assayed in vitro using a four-day-old primary culture of dispersed rat pituitary cells and compared with LRF. The levels of LH secreted over a 4-hour period in response to the application of peptides are assayed by specific radioimmunoassay for rat LH. The results of testing are expressed in Table I herebelow:

TABLE I

| TREATMENT | NANOGRAMS OF LH SECRETED |
|-----------|--------------------------|
| Control | 612 |
| 0.1 nM LRF | 1255 |
| 0.3 nM LRF | 1767 |
| 1.0 nM LRF | 2167 |
| 3.0 nM LRF | 2867 |
| 0.003 nM Ex. I | 885 |
| 0.01 nM Ex. I | 1345 |
| 0.03 nM Ex. I | 2150 |
| 0.1 nM Ex. I | 2225 |
| 0.3 nM Ex. I | 2667 |

The treatment procedure is repeated using the peptide prepared in Example II and the results set forth in Table II are obtained:

TABLE II

| TREATMENT | NANOGRAMS OF LH SECRETED |
|---|---|
| Control | 500 |
| 0.3 nM LRF | 631 |
| 1.0 nM LRF | 1001 |
| 3.0 nM LRF | 1496 |
| 0.003 nM Ex. II | 895 |
| 0.01 nM Ex. II | 1256 |
| 0.03 nM Ex. II | 2008 |

The peptide prepared in Example I has a relative potency, compared to LRF, of 12(5.8-24)—the confidence limits being shown in the parentheses. For the peptide prepared in Example II, the relative potency is 217(57-952). Based upon these tests, it can be seen that [D-His$^6$(im-Bzl)]-LRF has a potency about 12 times that of LRF and that [D-His$^6$(im-Bzl), Pro$^9$-NEt]-LRF has a potency of more than 200 times that of LRF.

The effectiveness of the peptide compositions prepared in Examples I and II is also tested in vivo, and the relative agonistic potencies of peptides determined in the in vitro assays reported above correlate well with the potencies obtained from in vivo tests. Comparison of the results shows that both peptide compositions are very significantly more potent than LRF when tested in vivo.

Based upon the foregoing, the peptides of the invention can be used to regulate fertility in male and female animals and human beings. High, frequency administrations of these peptides will inhibit fertility by blocking ovulation, including premature luteolysis and terminating pregnancy in females and in inhibiting spermatogenesis in males. Lower, intermittent administrations can restore fertility in those infertile states caused by LRF deficiency and can also allow timing of ovulation in normal females. The peptides can also be employed to reduce levels of sex steroids, and thus they can be used in the management of subjects with sex hormone dependent neoplasms. As earlier mentioned, the peptides can be administered by intravenous, subcutaneous, subligual, oral, intravaginal, intranasal or rectal routes. The high water solubility of these peptides permits higher concentrations to be dissolved in physiologic solutions.

Although the invention has been described with regard to its preferred embodiments, it should be understood that changes and modifications as would be obvious to one having the ordinary skill in this art may be made without departing from the scope of the invention which is set forth in the claims which are appended hereto.

Various features of the invention are emphasized in the claims which follow.

What is claimed is:

1. A compound selected from the class defined by the formulae:

p-Glu-His-Trp-Ser-Tyr-D-His(im-Bzl)-Leu-Arg-R and its nontoxic salts, and $X^1$-p-Glu-His($X^2$)-Trp-Ser($X^3$)-Tyr($X^4$)-D-His(im-Bzl)-Leu-Arg($X^5$)-Pro-$X^6$ wherein R is selected from the group consisting of Pro-Gly-NH$_2$ and Pro-NH-CH$_2$-CH$_3$;

$X^1$ is either hydrogen or an α-amino protecting group;

$X^2$ is a protecting group for the imidazole nitrogen atom selected from the group consisting of Tos, benzyl, trityl, 2,2,2-trifluoro-1-benzyloxycarbonyl-aminoethyl, 2,2,2-trifluoro-1tert-butyloxycarbonylaminoethyl and 2,4-dinitrothiophenyl;

$X^3$ is a protecting group for the alcoholic hydroxyl group of Ser selected from the group consisting of acetyl, benzoyl, tetrahydropyranyl, tert-butyl, trityl, benzyl and 2,6-dichlorobenzyl;

$X^4$ is a protecting group for the phenolic hydroxyl group of Tyr selected from the group consisting of tetrahydropyranyl, tert-butyl, trityl, benzyl, benzyloxycarbonyl, 4-bromobenzyloxycarbonyl and 2,6-dichlorobenzyl;

$X^5$ is protecting group for the nitrogen atoms of Arg selected from the group consisting of nitro, Tos, benzyloxycarbonyl, adamantyloxycarbonyl, and BOC, or is hydrogen; and $X^6$ is selected from the group consisting of dimethylamine, alkylamine of 1 to 5 carbon atoms, phenethylamine, O-CH$_2$-[resin support], Gly-O-CH$_2$-[resin support], and Gly-NH [resin support].

2. A compound in accordance with claim 1 wherein R is Pro-Gly-NH$_2$.

3. A compound in accordance with claim 1 wherein R is Pro-NH-CH$_2$-CH$_3$.

4. A method for regulating fertility and the production of gonadotropins and sex steroids in male and female mammalians comprising administering an effective amount of a peptide having the formula:

p-Glu-His-Trp-Ser-Tyr-D-His(im-Bzl)-Leu-Arg-R, wherein

R is selected from the group consisting of Pro-Gly-NH$_2$ and Pro-NH-CH$_2$-CH$_3$, or a nontoxic salt thereof.

5. A method in accordance with claim 4 wherein R is Pro-Gly-NH$_2$.

6. A method in accordance with claim 4 wherein R is Pro-NH-CH$_2$-CH$_3$.

* * * * *

UNITED STATES PATENT AND TRADEMARK OFFICE

CERTIFICATE EXTENDING PATENT TERM
UNDER 35 U.S.C. § 156

PATENT NO.     : 4,244,946

DATED          : January 13, 1981

INVENTOR(S)    : Jean E.F. Rivier et al.

PATENT OWNER   : The Salk Institute for Biological Studies

This is to certify that there has been presented to the

COMMISSIONER OF PATENTS AND TRADEMARKS an application under 35 U.S.C. § 156 for an extension of the patent term. Since it appears that the requirements of the law have been met, this certificate extends the term of the patent for the period of

TWO YEARS from the original expiration date of the patent, June 11, 1999, with all rights pertaining thereto as provided by 35 U.S.C. § 156(b).

I have caused the seal of the Patent and Trademark Office to be affixed this 25th day of April 1996.

Bruce A. Lehman
Assistant Secretary of Commerce and
   Commissioner of Patents and Trademarks